(12) United States Patent
Simpson et al.

(10) Patent No.: US 8,895,715 B2
(45) Date of Patent: Nov. 25, 2014

(54) S100B MINI-PROMOTERS

(75) Inventors: Elizabeth M. Simpson, Vancouver (CA); Wyeth W. Wasserman, Vancouver (CA); Robert A. Holt, Vancouver (CA); Steven J. Jones, Vancouver (CA); Daniel Goldowitz, Vancouver (CA); Elodie Portales-Casamar, Vancouver (CA); Cletus D'Souza, Vancouver (CA); Vikramjit Chopra, Vancouver (CA)

(73) Assignee: The University of British Columbia, Vancouver (CA)

( * ) Notice: Subject to any disclaimer, the term of this patent is extended or adjusted under 35 U.S.C. 154(b) by 887 days.

(21) Appl. No.: 12/387,842

(22) Filed: May 7, 2009

(65) Prior Publication Data

US 2009/0280568 A1     Nov. 12, 2009

Related U.S. Application Data (60) Provisional application No. 61/071,640, filed on May 9, 2008.

(51) Int. Cl.

| | | |
|---|---|---|
| C07H 21/00 | (2006.01) | |
| C07H 21/02 | (2006.01) | |
| C12N 15/00 | (2006.01) | |
| C12N 5/00 | (2006.01) | |
| C12N 5/02 | (2006.01) | |
| C12N 15/85 | (2006.01) | |
| C07K 14/47 | (2006.01) | |

(52) U.S. Cl.
CPC .............. *C07K 14/47* (2013.01); *C12N 2800/00* (2013.01); *C12N 2830/008* (2013.01); *C12N 15/85* (2013.01)
USPC ....... 536/24.1; 536/23.1; 435/320.1; 435/325

(58) Field of Classification Search
None
See application file for complete search history.

(56) References Cited

PUBLICATIONS

Xie, et al. (1992) "Domains of the Rat rDNA Promoter Must be Aligned Stereospecifically", Molecular and Cellular Biology, 12(3): 1266-75.*
Tsoporis, et al. (2002) "Regulation of the S100B Gene by [alpha-1]-adrenergic Stimulation in Cardiac Myocytes", AJP-Heart and Circulatory Physiology, 284: H193-H203.*
Castets; et al., "Transcriptional regulation of the human S100 beta gene." Molecular Brain Research (1997), 46 (1-2):208-16.
Deloulme; et al., "Nuclear expression of S100B in oligodendrocyte progenitor cells correlates with differentiation toward the oligodendroglial lineage and modulates oligodendrocytes maturation." Mol. Cell. Neurosci. (2004), 27 (4):453-65.
Hachem; et al., "Spatial and temporal expression of S100B in cells of oligodendrocyte lineage." Glia (2005), 51 (2):81-97.
Hagiwara; et al., "Regulation of the rat S100 beta gene expression: the role of the 2 kb 5'-upstream sequence in glial specific expression." Journal of Neuroscience Research (1995), 42(5):603-12.
Lin; et al., "Inhibiting S100B restores p53 levels in primary malignant melanoma cancer cells." The Journal of Biological Chemistry (2004), 279(32):34071-7.
Lyck; et al., "Immunohistochemical markers for quantitative studies of neurons and glia in human neocortex." Journal of Histochemistry & Cytochemistry (2008), 56(3):201-21.
Marshak, "S100 beta as a neurotrophic factor." Progress in Brain Research (1990), 86:169-81.
Rothermundt; et al, "S100B in brain damage and neurodegeneration." Microscopy Research and Technique (2003), 60(6):614-32.
Vives; et al., "Visualization of S100B-positive neurons and glia in the central nervous system of EGFP transgenic mice." The Journal of Comparative Neurology (2003), 457(4):404-19.

* cited by examiner

*Primary Examiner* — Robert M Kelly
(74) *Attorney, Agent, or Firm* — Bozicevic, Field & Francis LLP; Pamela J. Sherwood (57) ABSTRACT

Isolated polynucleotides comprising an S100B promoter are provided, where an S100B regulatory element is operably joined to an S100B basal promoter utilizing a non-native spacing between the promoter and regulatory elements. The promoter may be operably linked to an expressible sequence, e.g. reporter genes, genes encoding a polypeptide of interest, regulatory RNA sequences such as miRNA, siRNA, antisense RNA, etc., and the like. In some embodiments a cell comprising a stable integrant of an expression vector is provided, which may be integrated in the genome of the cell. The promoter may also be provided in a vector, for example in combination with an expressible sequence. The polynucleotides find use in a method of expressing a sequence of interest, e.g. for identifying or labeling cells, monitoring or tracking the expression of cells, etc.

18 Claims, 3 Drawing Sheets
(2 of 3 Drawing Sheet(s) Filed in Color)

S100B MINI-PROMOTERS

FIELD OF THE INVENTION

The invention relates to gene promoters and regulatory elements. More specifically, the invention relates to novel S100B promoter compositions and related methods.

BACKGROUND

S100B is a member of the S100 protein family. S100 protein is a low molecular weight protein found in vertebrates characterized by two calcium binding sites of the helix-loop-helix ("EF-hand type") conformation. There are at least 21 different types of S100 proteins. The name is derived from the fact that the protein is 100% soluble in ammonium sulfate at neutral pH. S100B is an acidic protein with a molecular weight of 21 kDa existing as a homodimer consisting of two beta subunits. The two monomers are configured in a twofold axis of rotation and are held together by disulfide bonds. S100B is involved in the regulation of energy metabolism in brain cells. S100B is produced primarily by astrocytes and exerts autocrine and paracrine effects on glia, neurons, and microglia. Furthermore, it interacts with many immunological functions of the brain (reviewed in Rothermundt et al. 2003).

Functional S100B promoter sequences have been identified and analyzed in several mammalian species. The structure of the human S100B gene and proximal promoter region was initially elucidated by Allore (1990). Castets et al. (1997) analyzed several human constructs containing different fragments of the human S100B promoter which revealed a complex pattern of regulation relating to different regions of the promoter. In this study, a number of positive and negative regulatory elements that are at least partially involved in regulating cell specific expression were identified in the region between −1012 and +697 (with +1 being defined as the first nucleotide in exon 1 of the S100B gene). Additionally, a negative regulatory element is thought to be located in the region between −4437 and −1012 of the upstream region, however the precise location of this element was not elucidated. This study highlighted the complexity of the regulation of this gene to allow specific cell specific expression of human S100B. Lin et al. (2004) analyzed p53 transcription factor binding sites and their effect on human S100B promoter activity in malignant melanoma cells.

Expression of S100B has been shown to be spatiotemporally associated with maturation of glial cells in mice (Deloulme et al. 2004; Raponi et al. 2007) and rats (Hagiwara and Sueoka 1995). In a separate study, an enhanced green fluorescent protein (EGFP) reporter was fused to the −1669/+3116 region of the mouse S100B gene, resulting in observed expression in both astrocytes and oligodendrocytes, an expression pattern that occurred in both a spatial and temporal fashion during mouse brain development (Vives et al. 2003). More recent data using this same expression construct further highlights the spatiotemporal expression pattern in both astrocytic and oligodendrocytic lineages in the mouse brain (Hachem et al. 2005). Analysis of expression patterns in humans have also revealed spatiotemporal expression during brain development, particularly in proliferating and mature astrocytes (Marshak 1990; Tiu et al. 2000). Antibodies raised to S100B have been shown to label primarily astrocytes in human brain (Lyck et al. 2008).

There exists a significant need for promoter elements which are capable of driving expression in specific cell types and/or in specific regions of the brain. Identification of minimal elements required for adequate expression and specificity will allow ease of use in expression constructs.

SUMMARY OF THE INVENTION

The present invention provides novel nucleic acid sequence compositions and methods, which relate to S100B promoters having a sequence other than a native S100B promoter.

In one embodiment of the invention, there is provided an isolated nucleic acid fragment comprising an S100B mini-promoter, wherein the S100B mini-promoter comprises an S100B regulatory element operably linked in a non-native conformation to an S100B basal promoter. The S100B promoter may have a nucleic acid sequence that is substantially similar in sequence and function to SEQ ID NO: 1. The S100B regulatory element may have a nucleic acid sequence that is substantially similar in sequence and function to SEQ ID NO: 2. The S100B basal promoter may have a nucleic acid sequence that is substantially similar in sequence and function to SEQ ID NO: 3. The S100B promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule.

In one embodiment, there is provided an expression vector comprising an S100B mini-promoter element, wherein the S100B mini-promoter element comprises an S100B regulatory element operably linked in a non-native conformation to an S100B basal promoter element. The S100B promoter may have a nucleic acid sequence which is substantially similar in sequence and function to SEQ ID NO: 1. The S100B regulatory element may have a nucleic acid sequence which is substantially similar in sequence and function to SEQ ID NO: 2. The S100B basal promoter may have a nucleic acid sequence which is substantially similar in sequence and function to SEQ ID NO: 3. The S100B promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may further comprise a genomic targeting sequence. The genomic targeting sequence may be HPRT.

In one embodiment, there is provided a method for selective expression of a gene, protein, RNA interference molecule or the like in a cell, the method comprising introducing into the cell a expression vector comprising an S100B mini-promoter element of the invention, wherein the S100B mini-promoter element comprises an S100B regulatory element operably linked in a non-native conformation to an S100B basal promoter element. Cells of interest include, without limitation, cells of the peripheral or central nervous system and progenitors thereof, e.g. embryonic stem cells, neural stem cells, neurons, glial cells, astrocytes, microgial cells, etc. The S100B promoter may have a nucleic acid sequence which is substantially similar in sequence and function to SEQ ID NO: 1. The S100B regulatory element may have a nucleic acid sequence which is substantially similar in sequence and function to SEQ ID NO: 2. The S100B basal promoter may have a nucleic acid sequence which is substantially similar in sequence and function to SEQ ID NO: 3. The S100B promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may thus further comprise a genomic targeting sequence. The genomic targeting sequence may be HPRT.

In one embodiment of the invention, there is provided a method for identifying or selectively labeling a cell, the method comprising introducing into the cell a expression vector comprising an S100B mini-promoter element operably linked to an expressible sequence, wherein the S100B mini-promoter element comprises an S100B regulatory element operably linked in a non-native conformation to an S100B basal promoter element, and wherein the expressible sequence comprises a reporter gene. The S100B promoter element may have a nucleic acid sequence substantially similar in sequence and function to SEQ ID NO: 1. The S100B regulatory element may have a nucleic acid sequence substantially similar in sequence and function to SEQ ID NO: 2. The S100B basal promoter element may have a nucleic acid sequence substantially similar in sequence and function to SEQ ID NO:3. In some embodiments, the cell is a peripheral or central nervous system cell or progenitors thereof, including, without limitation, embryonic stem cells, neural stem cells, glial cell, e.g. Bergmann glial cells, astrocytes, and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like.

In one embodiment of the invention, there is provided a method for monitoring or tracking the development or maturation of a cell, the method comprising: 1) introducing into the cell a expression vector comprising an S100B mini-promoter element operably linked to an expressible sequence, wherein the S100B mini-promoter element comprises an S100B regulatory element operably linked in a non-native conformation to an S100B basal promoter element, and wherein the expressible sequence comprises a reporter gene; and 2) detecting the expression of the reporter gene in the cell of in progeny of the cell as a means of determining the lineage, identity or developmental state of the cell or cell progeny. The S100B promoter element may have a nucleic acid sequence substantially similar in sequence and function to SEQ ID NO: 1. The S100B regulatory element may have a nucleic acid sequence substantially similar in sequence and function to SEQ ID NO: 2. The S100B basal promoter element may have a nucleic acid sequence substantially similar in sequence and function to SEQ ID NO: 3. In some embodiments, the cell into which the expression vector is initially introduced is a peripheral or central nervous system cell or progenitors thereof, including, without limitation, embryonic stem cells, neural stem cells, glial cell, e.g. Bergmann glial cells, astrocytes, and the like.

SHORT DESCRIPTION OF FIGURES

The patent or application file contains at least one drawing executed in color. Copies of this patent or patent application publication with color drawing(s) will be provided by the Office upon request and payment of the necessary fee.

DETAILED DESCRIPTION

The polynucleotide compositions of the present invention comprise a novel arrangement of S100B promoter elements (also referred to herein as S100B mini-promoters) as well as novel expression vectors comprising said arrangement of S100B promoter elements (or mini-promoters). The present invention also includes various methods of utilizing these novel S100B promoter (or mini-promoter) elements or expression vectors.

Provided is a sequence listing including certain of the S100B mini-promoters, wherein SEQ ID NO:1 comprises the human S100B mini-promoter (3892 bp). Nucleotides 1-2507 comprise the human S100B regulatory element; and nucleotides 2508-3892 comprise the human S100B basal promoter element. SEQ ID NO: 2 comprises the human S100B regulatory element, which corresponds to human genome position: chr.21 46867265-46864758. SEQ ID NO:3 comprises the human S100B basal promoter element, which corresponds to human genome position: chr.21 46850766-46849383.

The term 'S100B' refers to the gene that encodes the S100B protein, and includes the controlling regulatory elements, e.g. promoters and the like. S100B is referred to as S100beta, S100 calcium binding protein beta, S100 calcium binding protein B, and NEF. The protein encoded by this S100B is a member of the S100 family of proteins containing 2 EF-hand calcium-binding motifs. S100 proteins are localized in the cytoplasm and/or nucleus of a wide range of cells, and involved in the regulation of a number of cellular processes such as cell cycle progression and differentiation. The human homolog of S100B is encoded by the human gene identified as EntrezGene #6285, and is located at chromosomal location 21q22.3. The protein encoded by human S100B has the Protein Accession #P04271 (Swiss-Prot). Other mammalian S100B homologs include but are not limited to: Rattus norvegicus (EntrezGene #25742, Protein Accession #P04631), Mus musculus (EntrezGene #20203, Protein Accession #P50114).

The term 'promoter' refers to the regulatory DNA region which controls transcription or expression of a gene and which can be located adjacent to or overlapping a nucleotide or region of nucleotides at which RNA transcription is initiated. A promoter contains specific DNA sequences which bind protein factors, often referred to as transcription factors, which facilitate binding of RNA polymerase to the DNA leading to gene transcription. A 'basal promoter', also referred to as a 'core promoter', generally refers to a promoter that contains all the basic necessary elements to promote transcriptional expression of an operably linked polynucleotide. Eukaryotic basal promoters typically, though not necessarily, contain a TATA-box and/or a CAAT box. An 'S100B basal promoter', in the context of the present invention and as used herein, is a nucleic acid compound having a sequence with at least 65%, at least 70%, at least 80%, at least 85%, at least 90%, at least 95%, or at least 99% similarity to SEQ ID NO: 3, and which comprises at least 5, usually at least 8, and may comprise all 11 of the identified conserved sequences listed in Table 1. The S100B basal promoters of the present invention may comprise a TATA box such as that found at position −29 (relative to the transcriptional start site) of the native human S100B promoter and/or a CAAT box (in this case, a reverse CAAT box) such as that found at position −93 (relative to the transcriptional start site) of the native human S100B promoter, and these elements should be positioned relative to the transcriptional start site (+1) in a way that is reflective of the native sequence.

TABLE 1

List of conserved sequences in the human
S100B basal promoter - SEQ ID NO: 3. The start and end
coordinates of the sequences are relative to the full SEQ ID NO: 3 sequence.

| Start (relative to SEQ ID NO: 3) | End (relative to SEQ ID NO: 3) | Invariant sequence type |
|---|---|---|
| 79 | 116 | p53 validated binding site |
| 246 | 285 | Conserved sequence |
| 424 | 503 | Conserved sequence |
| 562 | 585 | Conserved sequence |
| 769 | 792 | Conserved sequence |
| 825 | 844 | Conserved sequence |
| 880 | 933 | Conserved sequence |
| 949 | 968 | Conserved sequence |
| 975 | 1146 | Conserved sequence |

TABLE 1-continued

List of conserved sequences in the human
S100B basal promoter - SEQ ID NO: 3. The start and end
coordinates of the sequences are relative to the full SEQ ID NO: 3 sequence.

| Start (relative to SEQ ID NO: 3) | End (relative to SEQ ID NO: 3) | Invariant sequence type |
|---|---|---|
| 1154 | 1173 | Conserved sequence |
| 1192 | 1218 | Conserved sequence |

A promoter may also include 'regulatory elements' which may also influence the expression or transcription by the promoter. Such regulatory elements encode specific DNA sequences which bind other factors, which may include but are not limited to enhancers, silencers, insulators, and/or boundary elements. An 'S100B regulatory element', in the context of the present invention and as used herein, is a nucleic acid compound having a sequence with at least 65%, at least 70%, at least 80%, at least 85%, at least 90%, at least 95%, or at least 99% similarity to SEQ ID NO: 2, and which comprises at least 20, usually at least 25, and may comprise all 27 of the identified conserved sequences listed in Table 2. The present invention provides, in certain embodiments as described herein, different promoters of the S100B gene. In some embodiments, the S100B promoter comprises an S100B regulatory element operably linked to an S100B basal promoter.

TABLE 2

List of conserved sequences in the human
S100B regulatory element - SEQ ID NO: 2. The start and end
coordinates of the sequences are relative to the full SEQ ID NO: 2 sequence.

| Start (relative to SEQ ID NO: 2) | End (relative to SEQ ID NO: 2) | Invariant sequence type |
|---|---|---|
| 85 | 105 | Conserved sequence |
| 141 | 160 | Conserved sequence |
| 212 | 231 | Conserved sequence |
| 317 | 344 | Conserved sequence |
| 415 | 447 | Conserved sequence |
| 495 | 514 | Conserved sequence |
| 531 | 553 | Conserved sequence |
| 562 | 582 | Conserved sequence |
| 603 | 624 | Conserved sequence |
| 651 | 710 | Conserved sequence |
| 720 | 746 | Conserved sequence |
| 806 | 829 | Conserved sequence |
| 931 | 966 | Conserved sequence |
| 1191 | 1210 | Conserved sequence |
| 1245 | 1287 | Conserved sequence |
| 1300 | 1341 | Conserved sequence |
| 1350 | 1375 | Conserved sequence |
| 1422 | 1445 | Conserved sequence |
| 1548 | 1577 | Conserved sequence |
| 1630 | 1658 | Conserved sequence |
| 1708 | 1730 | Conserved sequence |
| 1743 | 1783 | Conserved sequence |
| 1786 | 1807 | Conserved sequence |
| 1912 | 1938 | Conserved sequence |
| 2088 | 2158 | Conserved sequence |
| 2212 | 2231 | Conserved sequence |
| 2315 | 2341 | Conserved sequence |

The term 'operably linked', in the context of the present invention, means joined in such a fashion as to work together to allow transcription. In some embodiments of the invention, two polynucleotide sequences may be operably linked by being directly linked via a nucleotide bond. In this fashion, the two operably linked elements contain no intervening sequences and in being joined are able to direct transcription of an expression sequence. In other embodiments of the invention, two elements may be operably linked by an intervening compound, for instance a polynucleotide sequence of variable length. In such a fashion, the operably linked elements, although not directly juxtaposed, are still able to direct transcription of an expression sequence. Thus, according to some embodiments of the invention, one or more promoter elements may be operably linked to each other, and additionally be operably linked to a downstream expression sequence, such that the linked promoter elements are able to direct expression of the downstream expression sequence.

The term 'mini-promoter' refers to a promoter in which certain promoter elements are combined in a non-native conformation, usually in such a fashion as to reduce the overall size of the promoter compared to the native conformation. For example, after identification of critical promoter elements, using one or more of various techniques, the native sequences that intervene the identified elements may be partially or completely removed. Other non-native sequences may optionally be inserted between the identified promoter elements. A mini-promoter may provide certain advantages over native promoter conformations. For example, the smaller size of the mini-promoter may allow easier genetic manipulation, ie. for the design and/or construction of expression vectors or other recombinant DNA constructs. In addition, the smaller size may allow easier insertion of DNA constructs into host cells and/or genomes, ie. via transfection, transformation, etc. Other advantages of mini-promoters would be apparent to one of skill in the art. In some embodiments of the invention, there are thus provided novel S100B mini-promoters comprising an S100B regulatory element operably linked in a non-native conformation to an S100B basal promoter. In general the spacing between the S100B regulatory element and the S100B basal promoter is not more than about 15 KB, generally not more than about 10 KB, usually not more than about 1 KB, more often not more than about 500 nt, and may be not more than about 100 nt, and includes a direct joining of the two sequences.

The term 'expressible sequence' refers to a polynucleotide that is operably linked to a promoter element, such that the promoter element causes transcriptional expression of the expression sequence. An expressible sequence is typically linked downstream, on the 3'-end of the promoter element(s) in order to achieve transcriptional expression. The result of this transcriptional expression is the production of an RNA macromolecule. The expressed RNA molecule may encode a protein and may thus be subsequently translated by the appropriate cellular machinery to produce a polypeptide protein molecule. In some embodiments of the invention, the expression sequence may encode a reporter protein. Alternately, the RNA molecule may be an antisense, RNAi or other non-coding RNA molecule, which may be capable of modulating the expression of specific genes in a cell, as is known in the art.

The term 'RNA' as used in the present invention includes full-length RNA molecules, which may be coding or non-coding sequences, fragments, and derivatives thereof. For example, a full-length RNA may initially encompass up to about 20 Kb or more of sequence, and frequently will be processed by splicing to generate a small mature RNA. Fragments, RNAi, miRNA and anti-sense molecules may be smaller, usually at least about 18 nt. in length, at least about 20 nt in length, at least about 25 nt. in length, and may be up to about 50 nt. in length, up to about 100 nt in length, or more. RNA may be single stranded, double stranded, synthetic, isolated, partially isolated, essentially pure or recombinant. RNA compounds may be naturally occurring, or they may be altered such that they differ from naturally occurring RNA compounds. Alterations may include addition, deletion, substitution or modification of existing nucleotides. Such nucleotides may be either naturally occurring, or non-naturally occurring nucleotides. Alterations may also involve addition or insertion of non-nucleotide material, for instance at the end or ends of an existing RNA compound, or at a site that is internal to the RNA (ie. between two or more nucleotides).

The term 'nucleic acid' as used herein includes any nucleic acid, and may be a deoxyribonucleotide or ribonucleotide polymer in either single or double-stranded form. A 'polynucleotide' or 'nucleotide polymer' as used herein may include synthetic or mixed polymers of nucleic acids, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), and modified linkages (e.g., alpha anomeric polynucleotides, etc.). Also included are synthetic molecules that mimic polynucleotides in their ability to bind to a designated sequence via hydrogen bonding and other chemical interactions.

A 'purine' is a heterocyclic organic compound containing fused pyrimidine and imidazole rings, and acts as the parent compound for purine bases, adenine (A) and guanine (G). 'Nucleotides' are generally a purine (R) or pyrimidine (Y) base covalently linked to a pentose, usually ribose or deoxyribose, where the sugar carries one or more phosphate groups. Nucleic acids are generally a polymer of nucleotides joined by 3' 5' phosphodiester linkages. As used herein 'purine' is used to refer to the purine bases, A and G, and more broadly to include the nucleotide monomers, deoxyadenosine-5'-phosphate and deoxyguanosine-5'-phosphate, as components of a polynucleotide chain. A 'pyrimidine' is a single-ringed, organic base that forms nucleotide bases, such as cytosine (C), thymine (T) and uracil (U). As used herein 'pyrimidine' is used to refer to the pyrimidine bases, C, T and U, and more broadly to include the pyrimidine nucleotide monomers that along with purine nucleotides are the components of a polynucleotide chain.

It is within the capability of one of skill in the art to modify the sequence of a promoter nucleic acid, e.g. the provided basal promoter and regulatory sequences, in a manner that does not substantially change the activity of the promoter element, i.e. the transcription rate of an expressible sequence operably linked to a modified promoter sequence is at least about 65% the transcription rate of the original promoter, at least about 75% the transcription rate of the original promoter sequence, at least about 80%, at least about 90%, at least about 95%, at least about 99%, or more in a selected cell or suitable in vitro environment. Such modified sequences would be considered to be 'functionally similar' or to have 'functional similarity' or 'substantial functional similarity' to the unmodified sequence. Such modifications may include insertions, deletions which may be truncation of the sequence or internal deletions, or substitutions. The level of sequence modification to an original sequence will determine the 'sequence similarity' of the original and modified sequences. Modification of the promoter elements of the present invention in a fashion that does not significantly alter transcriptional activity, as described above would result in sequences with 'substantial sequence similarity' to the original sequence i.e. the modified sequence has a nucleic acid composition that is at least about 65% similar to the original promoter sequence, at least about 75% similar to the original promoter sequence, at least about 80%, at least about 90%, at least about 95%, at least about 99%, or more similar to the original promoter sequence. Thus, mini-promoter elements which have substantial functional and/or sequence similarity are herein described and are within the scope of the invention.

The nucleic acid sequence compositions provided in some embodiments of the invention contain p53 transcription factor binding sites, and it would be reasonable to expect that the binding sequence at these sites should not be altered if one expects to maintain the similar transcriptional expression from the unmodified sequence. For instance, the S100B regulatory element of the invention corresponding to SEQ ID NO: 3 contains a p53 transcription factor binding site at position 79-116 of SEQ ID NO: 3.

An 'RNA interference molecule', or 'RNA interference sequence' as defined herein, may include, but is not limited to, an antisense RNA molecule, a microRNA molecule or a short hairpin RNA (shRNA) molecule. Typically, RNA interference molecules are capable of target-specific modulation of gene expression and exert their effect either by mediating degradation of the mRNA products of the target gene, or by preventing protein translation from the mRNA of the target gene. The overall effect of interference with mRNA function is modulation of expression of the product of a target gene. This modulation can be measured in ways which are routine in the art, for example by Northern blot assay or reverse transcriptase PCR of mRNA expression, Western blot or ELISA assay of protein expression, immunoprecipitation assay of protein expression, etc.

An 'antisense RNA molecule', as used herein, is typically a single stranded RNA compound which binds to complementary RNA compounds, such as target mRNA molecules, and blocks translation from the complementary RNA compounds by sterically interfering with the normal translational machinery. Specific targeting of antisense RNA compounds to inhibit the expression of a desired gene may design the antisense RNA compound to have a homologous, complementary sequence to the desired gene. Perfect homology is not necessary for inhibition of expression. Design of gene specific antisense RNA compounds, including nucleotide sequence selection and additionally appropriate alterations, are known to one of skill in the art.

The term 'microRNA molecule', 'microRNA' or 'miRNA', as used herein, refers to single-stranded RNA molecules, typically of about 21-23 nucleotides in length, which are capable of modulating gene expression. Mature miRNA molecules are partially complementary to one or more messenger RNA (mRNA) molecules, and their main function is to down-regulate gene expression. Without being bound by theory, miRNAs are first transcribed as primary transcripts or pri-miRNA with a cap and poly-A tail and processed to short, 70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end. The remaining strand, known as the anti-guide or passenger strand, is degraded as a RISC complex substrate.

After integration into the active RISC complex, miRNAs base pair with their complementary mRNA molecules and induce mRNA degradation by argonaute proteins, the catalytically active members of the RISC complex. Animal miRNAs are usually complementary to a site in the 3' UTR whereas plant miRNAs are usually complementary to coding regions of mRNAs.

The term 'short hairpin RNA' or 'shRNA' refers to RNA molecules having an RNA sequence that makes a tight hairpin turn that can be used to silence gene expression via RNA interference. The shRNA hairpin structure is cleaved by the cellular machinery into siRNA, which is then bound to the RNA-induced silencing complex (RISC). This complex binds to and cleaves mRNAs which match the siRNA that is bound to it. shRNA is transcribed by RNA Polymerase III whereas miRNA is transcribed by RNA Polymerase II. Techniques for designing target specific shRNA molecules are known in the art.

An 'expression vector' is typically a nucleic acid molecule which is may be integrating or autonomous, (i.e. self-replicating), and which contains the necessary components to achieve transcription of an expressible sequence in a target cell, when introduced into the target cell. Expression vectors may include plasmids, cosmids, phage, YAC, BAC, mini-chromosomes, viruses, e.g. retroviruses, adenovirus, lentivirus, SV-40, and the like; etc. Many such vectors have been described in the art and are suitable for use with the promoters of the present invention. Expression vectors of the present invention include a promoter as described herein, operably linked to an expressible sequence, which may also be optionally operably linked to a transcription termination sequence, such as a polyadenylation sequence. The expression vector optionally contains nucleic acid elements which confer host selectivity, elements that facilitate replication of the vector, elements that facilitate integration of the vector into the genome of the target cell, elements which confer properties, for example antibiotic resistance, to the target cell which allow selection or screening of transformed cells and the like. Techniques and methods for design and construction of expression vectors are well known in the art.

It may be desirable, when driving expression of an expressible sequence with a particular promoter system, to have the expression occur in a stable and consistent manner. A factor that has been shown to affect expression is the site of integration of an expression vector or construct into the genome of the target cell, sometimes called 'position effects'. Such position effects may be caused by, for example, local chromatin structure which affects expression of sequences from that region of the genome. One method to control for position effects when integrating an expression vector or construct into the genome of a target cell is to include a 'genomic targeting sequence' in the vector or construct that directs integration of the vector or construct to a specific genomic site. As an example, the hypoxanthine phosphoribosyltransferase (HPRT) gene has been used successfully for this purpose (Bronson et al. 1996; Jasin et al. 1996). The HPRT gene has additional advantages as a genomic targeting sequence, for instance its concomitant use as a selectable marker system. Other genomic targeting sequences that may be useful in the present invention are described in the art, for instance (Jasin et al. 1996; van der Weyden et al. 2002). The genomic targeting signals as described herein are useful in certain embodiments of the present invention.

Introduction of nucleic acids or expression vectors may be accomplished using techniques well known in the art, for example microinjection, electroporation, particle bombardment, or chemical transformation, such as calcium-mediated transformation, as described for example in Maniatis et al. 1982, Molecular Cloning, A laboratory Manual, Cold Spring Harbor Laboratory or in Ausubel et al. 1994, Current protocols in molecular biology, Jolm Wiley and Sons.

S100B Promoters

The present invention herein provides novel S100B mini-promoter sequences which are capable of effecting transcriptional expression in a spatial and temporal fashion similar to naturally occurring S100B promoters. The S100B mini-promoters of the invention comprise S100B promoter elements joined in a non-native configuration, thus providing advantageous characteristics. Also provided are novel expression vector compositions comprising S100B mini-promoters which allow consistent specific spatiotemporal transcription of expression sequences. Also provided are novel methods utilizing these S100B mini-promoters and expression vectors.

The S100B promoters of the invention, as described herein, are referred to as 'mini-promoters' to reflect the fact that the mini-promoters comprise S100B promoter elements that are joined in a non-native configuration. In this context, native intervening sequences between promoter elements may have been partially or completely removed, and optionally may have been replaced with non-native sequences. In such a fashion, the natural spacing of the promoter elements, for instance the human S100B regulatory element corresponding to SEQ ID NO: 2 and the human S100B basal promoter element corresponding to SEQ ID NO: 3, or sequences with substantial functional and/or sequence equivalence, is altered. An advantage of such non-native mini-promoters is that the removal of native intervening sequences reduces the size of the mini-promoter while maintaining the functional activity of the promoter, thus improving the utility of the mini-promoter for various applications.

The inventors have demonstrated, as illustrated in the non-limiting Working Examples, that a human S100B mini-promoter having a sequence corresponding to SEQ ID NO: 1, and which is comprised of a human S100B regulatory element having a nucleic acid sequence corresponding to SEQ ID NO: 2 operably linked in a non-native conformation to a human S100B basal promoter having a nucleic acid sequence corresponding to SEQ ID NO: 3, is capable of directing expression of an expressible sequence which is operably linked downstream of the S100B promoter in specific cell types in different regions of the brain. The S100B regulatory element (SEQ ID NO: 2) and S100B basal promoter element (SEQ ID NO: 3) have sequences which are identical to those found upstream of the human S100B gene, found on chromosome 21 of the human genome. To place these sequences in context, SEQ ID NO: 2 corresponds to absolute genomic coordinates chr21:46864758-46867265 (strand-), while SEQ ID NO: 3 corresponds to absolute genomic coordinates chr21: 46849383-46850766 (strand-), where the genomic coordinates are derived from NCBI Build 36.1 human genome assembly of March 2006. In relative terms, SEQ ID NO: 2 corresponds to position −17882 to −15294, while SEQ ID NO: 3 corresponds to position −1302 to +81, where the position corresponding to +1 is defined as the first nucleic acid of exon 1 of the human S100B gene. It is within the skill of one in the art to locate and determine these relative positions based on published sequence information for this gene, for instance found in the GenBank or PubMed public databases. It is understood that these genomic coordinates and relative positions are provided for the purposes of context, and that if any discrepancies exist between published sequences and the sequence listings provided herein, then the sequence listings shall prevail.

Promoters of the present invention may be modified with respect to the native regulatory and/or native basal promoter sequence. In general, such modifications will not change the functional activity of the promoter with respect to cell-type selectivity; and to the rate of transcription in cells where the promoter is active. The modified promoter provide for a transcription rate in a cell of interest of an expressible sequence operably linked to a modified promoter sequence that is at least about 75% the transcription rate of the promoter sequence of SEQ ID NO:1, at least about 80%, at least about 90%, at least about 95%, at least about 99%, or more. Methods of assessing promoter strength and selectivity are known in the art, including, for example, expression of a reporter sequence in a cell in vivo or in vitro, and quantitating the reporter activity.

Modifications of interest include deletion of terminal or internal regions, and substitution or insertion of residues. Applicants have identified 38 conserved sequences in the S100B promoter (Table 1), where 27 such conserved sequences are present in the regulatory element, and 11 conserved sequences are present in the basal promoter. A promoter of interest in the present invention comprises at least 30, usually at least 35, and may comprise all 38 of the identified conserved sequences. Sequences set forth in SEQ ID NO:1 that are not conserved may be deleted or substituted, usually modifications that retain the spacing between conserved sequences is preferred. In general the spacing between the regulatory element and the basal promoter is not more than about 10 KB, generally not more than about 1 KB, usually not more than about 500 nt, and may be not more than about 100 nt, down to a direct joining of the two sequences.

TABLE 3

List of conserved sequences in SEQ ID NO: 1. The start and end coordinates of the sequences are relative to the full SEQ ID NO: 1 sequence.

| Start (relative to SEQ ID NO: 1) | End (relative to SEQ ID NO: 1) | Invariant sequence type |
|---|---|---|
| 85 | 105 | Conserved sequence |
| 141 | 160 | Conserved sequence |
| 212 | 231 | Conserved sequence |
| 317 | 344 | Conserved sequence |
| 415 | 447 | Conserved sequence |
| 495 | 514 | Conserved sequence |
| 531 | 553 | Conserved sequence |
| 562 | 582 | Conserved sequence |
| 603 | 624 | Conserved sequence |
| 651 | 710 | Conserved sequence |
| 720 | 746 | Conserved sequence |
| 806 | 829 | Conserved sequence |
| 931 | 966 | Conserved sequence |
| 1191 | 1210 | Conserved sequence |
| 1245 | 1287 | Conserved sequence |
| 1300 | 1341 | Conserved sequence |
| 1350 | 1375 | Conserved sequence |
| 1422 | 1445 | Conserved sequence |
| 1548 | 1577 | Conserved sequence |
| 1630 | 1658 | Conserved sequence |
| 1708 | 1730 | Conserved sequence |
| 1743 | 1783 | Conserved sequence |
| 1786 | 1807 | Conserved sequence |
| 1912 | 1938 | Conserved sequence |
| 2088 | 2158 | Conserved sequence |
| 2212 | 2231 | Conserved sequence |
| 2315 | 2341 | Conserved sequence |
| 2586 | 2624 | p53 validated binding site |
| 2753 | 2792 | Conserved sequence |
| 2931 | 3010 | Conserved sequence |

TABLE 3-continued

List of conserved sequences in SEQ ID NO: 1. The start and end coordinates of the sequences are relative to the full SEQ ID NO: 1 sequence.

| Start (relative to SEQ ID NO: 1) | End (relative to SEQ ID NO: 1) | Invariant sequence type |
| --- | --- | --- |
| 3069 | 3092 | Conserved sequence |
| 3276 | 3299 | Conserved sequence |
| 3332 | 3351 | Conserved sequence |
| 3387 | 3440 | Conserved sequence |
| 3456 | 3475 | Conserved sequence |
| 3482 | 3653 | Conserved sequence |
| 3661 | 3680 | Conserved sequence |
| 3699 | 3725 | Conserved sequence |

In some embodiments of the invention, there is thus provided an isolated nucleic acid fragment comprising an S100B mini-promoter, wherein the S100B promoter comprises an S100B regulatory element operably linked in a non-native conformation to an S100B basal promoter. In certain embodiments of the invention, the S100B promoter may have a nucleic acid sequence which is substantially similar in sequence and function to SEQ ID NO: 1. In some embodiments, the S100B regulatory element may have a nucleic acid sequence which is substantially similar in sequence and function to SEQ ID NO: 2. In some embodiments, the S100B basal promoter may have a nucleic acid sequence which is substantially similar in sequence and function to SEQ ID NO: 3. The S100B promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like.

It is an object of the present invention to provide means of expressing a gene, protein, RNA interference molecule or the like in a cell, tissue or organ. As such, the inventors thus provide novel expression vectors comprising S100B mini-promoters which are capable of accomplishing this task. In some embodiments of the invention, there is provided a expression vector comprising an S100B promoter element, wherein the S100B promoter element comprises an S100B regulatory element operably linked in a non-native conformation to an S100B basal promoter element. The S100B promoter element may have a nucleic acid sequence substantially similar in sequence and function to SEQ ID NO: 1. The S100B regulatory element may have a nucleic acid sequence substantially similar in sequence and function to SEQ ID NO: 2. The S100B basal promoter element may have a nucleic acid sequence substantially similar in sequence and function to SEQ ID NO: 3. The S100B promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expression vector may further comprise a genomic targeting sequence. The genomic targeting sequence may be HPRT.

The inventors have herein demonstrated that expression vectors comprising novel S100B mini-promoter elements are capable of directing transcription of an expression sequence in specific cell types, most notably glial cells, in specific regions of the brain. In some embodiments of the invention, there is thus provided a method for expressing a gene, protein, RNA interference molecule or the like in the targeted cells of the brain. Cells of interest include, without limitation, cells of the peripheral or central nervous system and progenitors thereof, e.g. embryonic stem cells, neural stem cells, neurons, glial cells, astrocytes, microgial cells, etc. The method comprises introducing into a glial cell or progenitor cell thereof an expression vector comprising an S100B mini-promoter element, wherein the S100B mini-promoter element comprises an S100B regulatory element operably linked in a non-native conformation to an S100B basal promoter element. The S100B promoter element may have a nucleic acid sequence substantially similar in sequence and function to SEQ ID NO: 1. The S100B regulatory element may have a nucleic acid sequence substantially similar in sequence and function to SEQ ID NO: 2. The S100B basal promoter element may have a nucleic acid sequence substantially similar in sequence and function to SEQ ID NO: 3. The S100B promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expression vector may thus further comprise a genomic targeting sequence. The genomic targeting sequence may be HPRT.

In other embodiments of the invention, there is provided a method for identifying or labeling a cell, the method comprising introducing into the cell a expression vector comprising an S100B mini-promoter element operably linked to an expressible sequence, wherein the S100B mini-promoter element comprises an S100B regulatory element operably linked in a non-native conformation to an S100B basal promoter element, and wherein the expressible sequence comprises a reporter gene. The S100B promoter element may have a nucleic acid sequence substantially similar in sequence and function to SEQ ID NO: 1. The S100B regulatory element may have a nucleic acid sequence substantially similar in sequence and function to SEQ ID NO: 2. The S100B basal promoter element may have a nucleic acid sequence substantially similar in sequence and function to SEQ ID NO: 3. The inventors have demonstrated that expression vectors comprising certain human S100B promoter elements are capable of expression in glial cell types in specific regions of the brain. In some embodiments, the cell is a peripheral or central nervous system cell or progenitors thereof, including, without limitation, embryonic stem cells, neural stem cells, glial cell, e.g. Bergmann glial cells, astrocytes, and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like.

In further embodiments of the invention, there is provided a method for monitoring or tracking the development or maturation of a cell in the glial cell lineage. The method comprises: 1) introducing into a progenitor to a glial cell, e.g. an embryonic stem cells, neural stem cell, glial progenitor cell, glial cell, etc., cell an expression vector comprising an S100B mini-promoter element operably linked to an expressible sequence, wherein the S100B mini-promoter element comprises an S100B regulatory element operably linked in a non-native conformation to an S100B basal promoter element, and wherein the expressible sequence comprises a reporter gene; and 2) detecting the expression of the reporter gene glial cell progeny of the cells as a means of determining the lineage, identity or developmental state of the cell or cell progeny. In such a fashion, one may be able to follow the development of a parent cell as it differentiates into more mature cells. As an example, one could introduce a expression vector comprising the aforementioned S100B promoter elements into a pluripotent stem cell, monitor the expression of the reporter gene that is being expressed by the S100B promoter elements during the maturation and differentiation of the stem cell and thus determine the state of maturation, for instance in the differentiation of the pluripotent stem cell into a glial cell. The inventors have demonstrated that the S100B promoter elements described herein cause transcriptional expression in certain glial cell types, and so detection of reporter gene expression in a cell would thus be indicative of the cellular identity of the cell as being a glial cell.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

WORKING EXAMPLES

General Methods

Expression vector. The nucleic acid fragment corresponding to SEQ ID NO: 1 was inserted into the multiple cloning site of the pEMS1306 (see FIG. 1) to produce the expression vector S100B-C.

Derivation of mEMS1204 embryonic stem cells. Blastocysts were obtained from natural mating of B6-Hprt1$^{b-m3}$ females to 129-ROSA26 males at 3.5 dpc. Blastocysts were flushed from uterine horns as per (Hogan et al. 1994), cultured in EmbryoMax® KSOM with ½ Amino Acids, Glucose and Phenol Red (Cat #MR-121, Millipore/Chermicon, Temecula, Calif.) for 3-5 h, and then transferred onto mitomycin C (mitC; Cat#M4287, Sigma, Oakville, ON) mitotically inactivated B6-Hprt1$^{b-m3}$, B6129F1, or 129 mouse embryonic feeders (MEFs) derived from 13.5-day post-coital embryos (Ponchio et al. 2000) in 96-well plates containing KSR-ESC (Knockout™ D-MEM, Cat#10829-018, Invitrogen, Burlington, ON) with 2 mM L-glutamine (Cat#25030-081, Invitrogen, Burlington, ON), 0.1 mM MEM nonessential amino acid solution (Cat#11140-050, Invitrogen, Burlington, ON) and 16% Knockout™ Serum Replacement (Cat#10828-028, Invitrogen, Burlington, ON)) media (MEF media was replaced 3-5 hour prior to transfer).

Blastocysts were cultured as per (Cheng et al. 2004) with the following modifications: Cells were cultured for 7-9 days in KSR-ESC with minimal disturbance (checked on day 2 to determine if the blastocysts had 'hatched' out of the zona pellucida) and no media changes. Blastocysts which hatched and had a well developed ICM (inner cell mass) were treated with 20 µl 0.25% trypsin-EDTA (Invitrogen, Burlington, ON) for 5 min at 37° C., triturated with a 200 µl pipetman, inactivated with 30 µl 0.5 mg/ml soybean trypsin inhibitor (Invitrogen, Burlington, ON), and brought up to 200 µl with KSR-ESC, then transferred individually to a 24-well MEF plate containing 1800 µl KSR-ESC, for a total volume of 2 ml:

Beginning 4 days later, KSR-ESC media was replaced with FBS-ESC media (DMEM (Cat #11960-069, Invitrogen, Burlington, ON) with 2 mM L-glutamine (Invitrogen, Burlington, ON), 0.1 mM MEM nonessential amino acid solution (Invitrogen, Burlington, ON), 16% ES Cell Qualified fetal bovine serum (FBS, Invitrogen, Burlington, ON) and 0.01% β-mercaptoethanol (Sigma, Oakville, ON) in 25%, 50%, 75% proportions (respectively) to adapt the cells to FBS containing media.

On day 7 the cells were trypsinized to one well of a 24 well plate containing 1 ml of 100% FBS-ESC media, with daily media replacement. Once confluent, wells containing ESC colonies were expanded 3×24 wells (with MEFs), then passaged to 3×24 (with MEFs) and 3×12 well (plastic—no MEFs) for DNA analysis. Once confluent, the 3×24 wells were combined, aliquoted (3 vials), and frozen in ESC-freeze media (50% FBS, 40% FBS-ESC media, 10% DMSO (Sigma, Oakville, ON), and the 3×12 well treated with lysis buffer (Fisher Scientific, Ottawa, ON), mixed and aliquoted. Cultures were genotyped for X & Y chromosomes (Clapcote and Roder 2005), Gt(ROSA)26Sor$^{tm1Sor}$ and WT alleles and Hprt1$^{b-m3}$ and WT alleles. B6129F1-Gt(ROSA)26Sor$^{tm1Sor}$/+, Hprt1$^{b-m3}$/Y and B6129F1-Gt(ROSA)26Sor$^{tm1Sor}$+/+, Hprt1$^{b-m3}$/Y cell lines were identified.

Knock-in at the Hprt1 locus. The S100B-C plasmid DNA was purified with Qiagen Maxi Kit (Qiagen, Mississauga, ON), resuspended in 10:1 Tris-EDTA (TE, pH7.0) buffer, and linearized with I-SceI (New England Biolabs, Pickering, ON). Linearized plasmid DNA was resuspended in 85 µl of TE (10:0.1) to a final concentration of 187.5 ng/µl. mEMS1204 ESCs were grown to confluence on 4-6 T75 flasks of mitC treated Hprt1$^{b-m3}$ mouse embryonic feeders (MEFs) in FBS-ESC media. ESCs (1.7–2.5×10$^7$) in 720 µl 1×PBS were added to the linearized DNA and electroporated in a 4 mm electroporation cuvette (Bio-Rad Genepulser, Mississauga, ON), at 240 V, 50 µF, 6-10 msec pulse, immediately resuspended in a total volume of 5 ml of FBS-ESC media and plated onto 5×100 mm dishes of mitC B6129F1 MEFs in a total volume of 12 ml/100 mm dish. 24-36 h post-electroporation, correctly targeted homologous recombinants were selected for using HAT media (FBS-ESC media containing 1×HAT ((0.1 mM sodium hypoxanthine, 0.4 mM aminopterin, 0.16 mM thymidine), Cat#21060-017, Invitrogen, Burlington, ON). HAT media was changed every day for the first 3 days, and then every 3$^{rd}$ day thereafter, for up to 10 days. Individual colonies were counted and, typically, no more than 2 isolated colonies were picked per 100 mm dish to optimize for independent homologous recombination events. These colonies were expanded under standard protocols for verification of the desired recombination event.

Derivation of knock-in mice. Chimeric mice from untargeted and targeted ESCs were generated by microinjection (Hogan et al. 1994) into B6 (E14TG2a derived) and B6-Alb (E14TG2a and mEMS1204 derived) E3.5 blastocysts, or co-culture (Lee et al. 2007) with diploid ICR (Charles River, Wilmington Wash. Stock#022) E2.5 morula (cultured overnight to the blastocyst stage), followed by implantation into the uterine horns of 2.5 day pseudopregnant ICR females. Chimeras were identified and coat color chimerism determined as outlined below.

Male chimeras derived from the E14TG2a cell lines were mated with B6 or B6-Alb females, and germline transmission was identified in the former case by the transmission of the dominant $A^w$ (nonagouti; white bellied agouti) allele, making the progeny appear brown with a cream belly, or in the later case by the combination of $A^w$ and $Tyr^{c-ch}$ (tyrosinase; chinchilla), making the progeny appear golden. Non-germline progeny from the cross to B6 were homozygous for the recessive a (nonagouti; nonagouti) allele and appeared black, whereas non-germline progeny from the cross to B6-Alb were homozygous for the recessive $Tyr^c$ (tyrosinase; albino) allele and appeared white.

Male chimeras derived from the mEMS1204 cell lines were mated with B6-Alb females, and germline transmission identified by the presence of the dominant $Tyr^+$ (tyrosinase; wild type) and the $A^w$ (nonagouti; white bellied agouti) or a (nonagouti; nonagouti) alleles making the progeny appear brown with a cream belly or black, respectively. Non-germline progeny were homozygous for the recessive $Tyr^{c-2J}$(tyrosinase; albino 2 Jackson) allele and appear white. All germline female offspring should carry the knock-in X Chromosome and were mated with B6 males. N2 offspring were analyzed for the presence of the KI allele by PCR.

Determination of coat color chimerism. E14TG2a- and mEMS1204-derived chimeras were identified and level of coat color chimerism determined as follows. E14TG2a ESCs, homozygous for $A^w$ and $Tyc^{c-ch}$ as they are derived from the 129/OlaHsd strain (Hooper et al. 1987a; Hooper et al. 1987b), will produce chimeras with cream/chinchilla and agouti patches on a black background when injected into B6 blastocysts. The cream/chinchilla patches result from melanocytes derived solely from the ESCs ($A^w/A^w$, $Tyr^{c-ch}/Tyr^{c-ch}$), whereas agouti patches result from melanocytes that are a mixture of ESC ($A^w/A^w$, $Tyr^{c-ch}/Tyr^{c-ch}$) and host (a/a, $Tyr^+/Tyr^+$). However, E14TG2a ESCs, when injected into B6-Alb (a/a, $Tyr^c/Tyr^c$) produce chimeras with chinchilla and light chinchilla coat color patches on a white background. The former is derived solely from the ESCs ($A^w/A^w$, $Tyr^{c-ch}/Tyr^{c-ch}$), whereas the latter is again a mix of the ESC ($A^w/A^w$, $Tyr^{c-ch}/Tyr^{c-ch}$) and host (a/a, $Tyr^c/Tyr^c$). mEMS1204-derived chimeras were identified and coat color chimerism determined in the same manner.

mEMS1204 ESCs, heterozygous $A^w$/a and homozygous for the wild type $Tyr^+$ alleles will produce chimeras with agouti and black patches on a white background when injected into B6-Alb blastocysts. The agouti patches result from melanocytes derived solely from the ESCs ($A^w$/a, $Tyr^+/Tyr^+$), whereas 'black' patches result from melanocytes that are a mixture of ESC ($A^w$/a, $Tyr^+/Tyr^+$) and host (a/a, $Tyr^{c-2J}/Tyr^{c-2J}$).

For E14TG2a injections into B6 and mEMS1204 injections into B6-Alb, overall chimerism was calculated by summing the percent of coat color patches derived solely from the ESC, plus half the percent of the ESC+ host areas, where we conservatively estimated that half the melanocytes derive from the ESC and half from the host. For E14TG2a injections into B6-Alb, the similarity between chinchilla and light chinchilla on a white background presented difficulty when attempting to estimate overall coat color chimerism. As such, we estimated the percent chimerism based solely on the total chimerism observed when compared to a white mouse, resulting in slightly inflated overall percent chimerism for this small cohort of mice.

Immunohistochemistry and Immunofluorescence. Adult male chimeric and age matched control mice were perfused with 4% paraformaldehyde (PFA) as previously described (Young et al. 2002). Whole brains were dissected out and post-perfusion immersion fixed with PFA for 2-3 hours at 4° C. Brains were then transferred to 20% sucrose at 4° C. overnight with gentle shaking. The brains were cryostat sectioned sagittally at 12-14 µm and mounted on superfost-plus slides (Cat#12-550-15, ThermoFisher Scientific, Waltham, Mass.). EGFP expression was detected by direct fluorescence of EGFP or by indirect immunofluorescence with anti-GFP antibodies (Abcam, Cambridge, Mass.) using a BioRad confocal laser scanning microscope (CLSM, BioRad, Hercules, Calif.).

For double label immunofluorescence analyses to determine cell types in the cerebellum, anti-GFAP was used in conjunction with direct EGFP fluorescence and imaged by CLSM (Liu et al. 2007). In brief, slide mounted brain sections, were permeabilized with phosphate buffered saline containing 0.1% triton-X100 (PBST), blocked with PBST containing 5% normal horse serum and 1% BSA, then incubated with primary antibodies overnight at room temperature in a humid chamber. Following three washes with PBST, the tissue were incubated with secondary antibodies (goat anti-rabbit-Alexa-594 conjugate, Molecular Probes, Eugene, Oreg.). The slides were counterstained with TOTO3/DAPI (1 µM each) for labeling all nuclei in confocal images. Bright field analyses were also conducted following immunocytochemical detection of anti-GFP using the Vectastain ABC kit and DAB as the chromogen to give a brown reaction product following the manufacturer's directions. Bright field images were visualized on a Zeiss Axiovert microscope and Axiovision Software (Carl Zeiss Microimaging, Thornwood, N.Y.).

Figure 1:
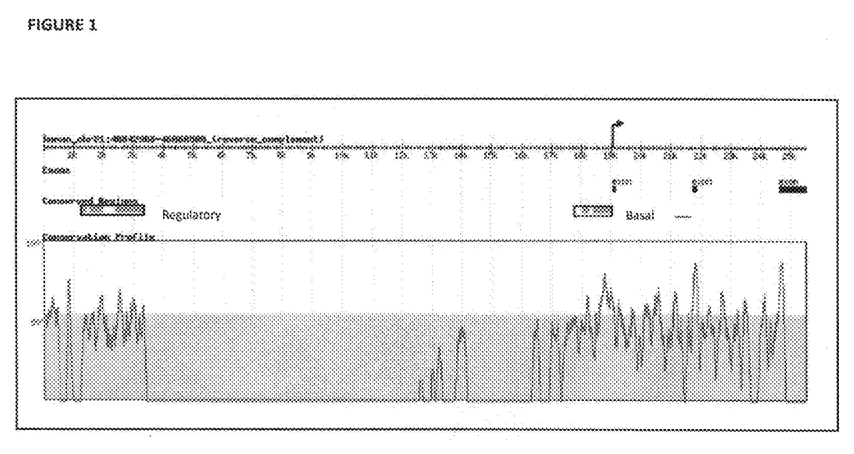
FIG. 1. From top to bottom, the human genomic sequence of S100B located on chromosome 21 with an arrow pointing to the transcription start site, the gene exons as black boxes, the non-coding conserved regions as blue boxes with open black boxes defining the promoter elements referred to in the present invention, the conservation profile between the human and mouse S100B sequences with the grey area delineating the 54% threshold used.

Selection of S100B promoter elements. Cross-species comparisons, or phylogenetic footprinting, were identified as a means to predict regulatory regions. The two mammalian species with the best evolutionary distance to use this approach are human and mouse. In the specific case of S100B, we computed the conservation level between human and mouse, taking into consideration the non-coding sequence located between the end of the upstream gene (PRMT2) and the end of S100B, including all intron sequences. Due to a lot of repeats in this area, the conservation is sparse and we set up a threshold of 54% of identity to select our candidate regulatory regions (FIG. 1). The S100B basal promoter (SEQ ID NO: 3) and regulatory region (SEQ ID NO: 2) were chosen based on these criteria.

Figure 2:
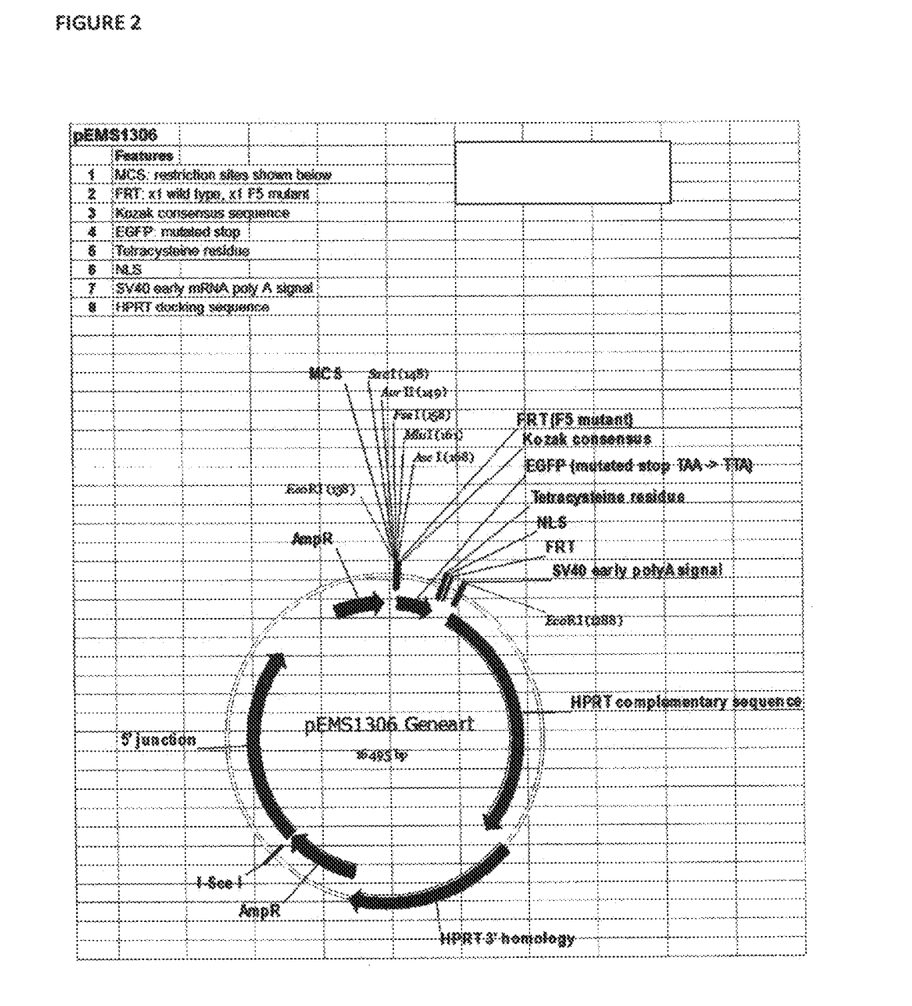
FIG. 2—DNA expression vector (pEMS1306) into which S100B promoter elements were inserted for expression studies. The S100B promoter with a nucleic acid sequence corresponding to SEQ ID NO: 1 was inserted into the multiple cloning site (MCS) of the pEMS1306 vector such that it became operably linked to the enhanced green fluorescent protein (EGFP) reporter gene. The final construct, called S100B-C, also contained the HPRT genomic targeting sequence, an ampicillin resistance gene (AmpR) for screening, and a transcriptional termination sequence (SV40 polyA), as well as other elements necessary for vector replication and gene expression.
Figure 3:
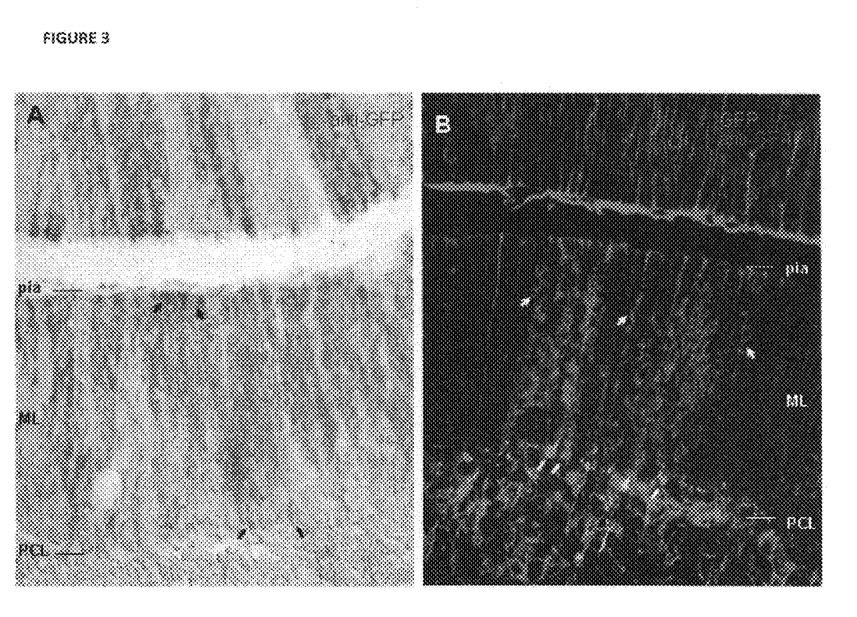
FIG. 3. A 14.5% chimera (tEMS 1561) from the S100B-C minipromoter (pEMS1384) strain shows specific staining in the cerebellum, labeling Bergman glial cells. A) Brightfield micrograph from the cerebellum. Anti-GFP staining (brown DAB reaction product) reveals radial processes of Bergman glia as well as in the cell bodies (small arrowheads) and pial endfeet (large arrowheads) in a clearly chimeric pattern (i.e. only a subpopulation of cells are labeled). B) Confocal laser scanning micrograph of a thin optical section in the cerebellum. Double label in the cerebellum of GFP fluorescence (green) and anti-GFAP immunofluorescence (red) clearly shows similar chimeric staining in the Bergman glia. GFP fluorescence highlights Bergman glial cell bodies (small arrowheads) and decorates processes (large arrowheads) that follow the GFAP (red) positive GFAP-positive radial processes. PCL, Purkinje cell layer; ML Molecular Layer, pia, apical pial surface.

Expression of reporter in glial cells by S100B-C promoter element. The S100B-C DNA expression vector (FIG. 2) comprising the S100B promoter element corresponding to SEQ ID NO: 1 (which is itself comprised of SEQ ID NO: 2 linked to SEQ ID NO: 3) was introduced into mouse embryonic stem cells (ESCs) at the HPRT locus. The ESCs were used to generate genetically modified mice containing S100B-C. Immunohistochemical and immunofluorescence analysis of mouse brain tissue slices revealed EGFP reporter expression in the Bergmann glial cells of the cerebellum (FIG. 3).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

Bronson, S. K., E. G. Plaehn, et al. (1996). "Single-copy transgenic mice with chosen-site integration." *Proc Natl Acad Sci USA* 93(17): 9067-72.

Castets, F., W. S. Griffin, et al. (1997). "Transcriptional regulation of the human S100 beta gene." *Brain Res Mol Brain Res* 46(1-2): 208-16.

Deloulme, J. C., E. Raponi, et al. (2004). "Nuclear expression of S100B in oligodendrocyte progenitor cells correlates with differentiation toward the oligodendroglial lineage and modulates oligodendrocytes maturation." *Mol Cell Neurosci* 27(4): 453-65.

Hachem, S., A. Aguirre, et al. (2005). "Spatial and temporal expression of S100B in cells of oligodendrocyte lineage." *Glia* 51(2): 81-97.

Hagiwara, N. and N. Sueoka (1995). "Regulation of the rat S100 beta gene expression: the role of the 2 kb 5'-upstream sequence in glial specific expression." *J Neurosci Res* 42(5): 603-12.

Hogan, B., R. Beddington, et al. (1994). *Manipulating the mouse.* Cold Spring Harbor, Cold Spring Harbor Laboratory Press.

Hooper, M., K. Hardy, et al. (1987a). "HPRT-deficient (Lesch-Nyhan) mouse embryos derived from germline colonization by cultured cells." *Nature* 326(6110): 292-5.

Hooper, M., K. Hardy, et al. (1987b). "HPRT-deficient (Lesch-Nyhan) mouse embryos derived from germline colonization by cultured cells." *Nature* 326: 292-295.

Jasin, M., M. E. Moynahan, et al. (1996). "Targeted transgenesis." *Proc Natl Acad Sci USA* 93(17): 8804-8.

Lee, K. H., C. K. Chuang, et al. (2007). "An alternative simple method for mass production of chimeric embryos by coculturing denuded embryos and embryonic stem cells in Eppendorf vials." *Theriogenology* 67(2): 228-37.

Lin, J., Q. Yang, et al. (2004). "Inhibiting S100B restores p53 levels in primary malignant melanoma cancer cells." *J Biol Chem* 279(32): 34071-7.

Lyck, L., I. Dalmau, et al. (2008). "Immunohistochemical markers for quantitative studies of neurons and glia in human neocortex." *J Histochem Cytochem* 56(3): 201-21.

Marshak, D. R. (1990). "S100 beta as a neurotrophic factor." *Prog Brain Res* 86: 169-81.

Raponi, E., F. Agenes, et al. (2007). "S100B expression defines a state in which GFAP-expressing cells lose their neural stem cell potential and acquire a more mature developmental stage." *Glia* 55(2): 165-77.

Rothermundt, M., M. Peters, et al. (2003). "S100B in brain damage and neurodegeneration." *Microsc Res Tech* 60(6): 614-32.

Tiu, S. C., W. Y. Chan, et al. (2000). "Differential expression of S100B and S100A6(1) in the human fetal and aged cerebral cortex." *Brain Res Dev Brain Res* 119(2): 159-68.

van der Weyden, L., D. J. Adams, et al. (2002). "Tools for targeted manipulation of the mouse genome." *Physiol Genomics* 11 (3): 133-64.

Vives, V., G. Alonso, et al. (2003). "Visualization of S100B-positive neurons and glia in the central nervous system of EGFP transgenic mice." *J Comp Neurol* 457(4): 404-19.

Young, K. A., M. L. Berry, et al. (2002). "Fierce: a new mouse deletion of Nr2e1; violent behaviour and ocular abnormalities are background-dependent." *Behav Brain Res* 132(2): 145-58.

---

What is claimed is:

1. An isolated polynucleotide comprising an S100B regulatory element having at least 95% sequence identity to SEQ ID NO:2 wherein the sequence elements at SEQ ID NO:2 residues 85-105; residues 141-160; residues 212-231; residues 317-344; residues 415-447; residues 495-514; residues 531-553; residues 562-582; residues 603-624; residues 651-710; residues 720-746; residues 806-829; residues 931-966; residues 1191-1210; residues 1245-1287; residues 1300-1341; residues 1350-1375; residues 1422-1445; residues 1548-1577; residues 1630-1658; residues 1708-1730; residues 1743-1783; residues 1786-1807; residues 1912-1938; residues 2088-2158; residues 2212-2231; and residues 2315-2341 are each conserved and present in said polynucleotide, operably joined to an S100B basal promoter having at least 95% sequence identity to SEQ iD NO:3 wherein the sequence elements at SEQ ID NO:3, residues 79-116; residues 246-285; residues 424-503; residues 562-585; residues 769-792; residues 825-844; residues 880-933; residues 949-968; residues 975-1146; residues 1154-1173; and residues 1192-1218 are each conserved and present in said polynucleotide, wherein the S100B regulatory element and the S100B basal promoter are joined through a non-native spacing of not more than 1 kb between the basal promoter and the regulatory element.

2. The isolated polynucleotide of claim 1, operably linked to an expressible sequence.

3. A vector comprising the isolated polynucleotide of claim 2.

4. A cell comprising the isolated polynucleotide of claim 1.

5. The cell of claim 4, wherein the vector comprises an expressible sequence operably linked to the S100B basal promoter.

6. The cell of claim 5, wherein the vector is stably integrated into the genome of the cell.

7. The cell of claim 6, wherein the cell is a stem cell.

8. The cell of claim 6, wherein the cell is a glial cell.

9. A method of expressing a sequence of interest, the method comprising operably linking the sequence of interest to the polynucleotide of claim 1, thereby forming an expressible sequence; and introducing into a cell permissive for expression from the S100B promoter, the the expressible sequence, wherein the sequence of interest is expressed in the cell permissive for expression.

10. An isolated polynucleotide having at least 95% sequence identity to SEQ ID NO:1.

11. The isolated polynucleotide of claim 10, operably linked to an expressible sequence.

12. A vector comprising the isolated polynucleotide of claim 11.

13. A cell comprising the isolated polynucleotide of claim 10.

14. The cell of claim 13, wherein the isolated polynucleotide having at least 95% sequence identity to SEQ ID NO: 1 is operably linked to an expressible sequence.

15. The cell of claim 14, wherein the isolated polynucleotide having at least 95% sequence identity to SEQ ID NO: 1 is stably integrated into the genome of the cell.

16. The cell of claim 15, wherein the cell is a stem cell.

17. The cell of claim 15, wherein the cell is a glial cell.

18. A method of expressing a sequence of interest, the method comprising operably linking the sequence of interest to the polynucleotide of claim 10, thereby forming an expressible sequence; and introducing into a cell permissive for expression from the S100B promoter, the expressible sequence, wherein the sequence of interest is expressed in the cell permissive for expression.

* * * * *

SEQUENCE LISTING

```
<160> NUMBER OF SEQ ID NOS: 3

<210> SEQ ID NO 1
<211> LENGTH: 3892
<212> TYPE: DNA
<213> ORGANISM: H. sapiens

<400> SEQUENCE: 1
cagatgtgag ttaagcagtt tgaacaatcg attgattaga cttttgtggc tgctcatttg      60
ggcatgtggc cgagtactgt gctgtcctgg cccacagcgt cctacaggaa gggacgggct     120
gtaagacgtg ggatcttctg aagtcgtcaa atgaaaaaca ctcctgttga gtgaaaaaac     180
aaataggcta atcctatgat tttttaaaca tttaaacctg acatgatttt attgcaaatt     240
tccaagaatc cttaaaagtt ataaaaagca taatcaaaat aaatatctgt gacagagttc     300
tacaaaaggg aaaactcagt tttccttttg agatcttgcc ccagcatcag ttcaaacact     360
tcctcatata tttcaccaag actcagttcc tgagcaagaa accacaggca cagcaagtgc     420
catgaaaagc ggctttgtgt ggggtgggct cttcacactc caatctccac ttccttctca     480
aggcctcaaa aaaagttgaa aaatgaaaac aaaagccctg ctgtgttgag ctgggctctg     540
gcgttgccat ggacccaggg caaacagcgg tgctcctgct ctgcccccgg ctcagctcat     600
gctgggcctg cacttctgga agggagcatg gactttgaa tgactggtta gaacccaaat      660
gaattaatgg aatttgacat agttcaaaaa taataaaatg tgatacccat gaaatgctga     720
tattctgcct taatttgcca gattggggc ctcctggatt tagagtattc taaagtagcc      780
agtaggttca ctctgcccctt ttagacctaa tatatctggc tcagaaagaa gtctctgtcc    840
```

```
ctctgctatt tgctgttctt tgctttgccc agtctgactc ctgccagctc caggttctgc    900
agacaagaac agtaactttt ataataataa taatgactcc caagtgagtg cattgggccc    960
ttcacgtgtg tctgtatgtg tgcacatgta tgtgcgtgtc aatttccttt actcctccta   1020
cagccctctc aggggtgcag cttttttct gtcttttact cagcctgaga aaggttgtcg   1080
tttgacaagg tttgttcaga ggtcggatct gaatccagct ccaaggcccc agcacccaag   1140
ccctgacccc atggctgcct gctggctggg agtggcattc tttagaacag gaaaggcagt   1200
gagttctcat tgcatcaata cttgcatttg ctacaacaga agcttttgt ctcttcctca   1260
cattccttta gaacacaagc ctccttttct gcctgtggcc atcggtcact ggagtcagcc   1320
tcgtgagtgg cttggtggcg gatggcaccg tcctttgtgg gagaaaacaa tgttgctgcc   1380
caggcctttc tggaatgacc ccttcccacc cctgaccag ccccagcaag gcccggggct   1440
ggctgcctag ttgattggag ccaagagttt gctgaatgga tgaagggaga agggacatcc   1500
aagtgactga agaagatctt aacagaagat tgatatattc aaatagaggc ccctgttgac   1560
ccacaagctc cttcgtgctc tggcctgggc aggcagcact gttgcttggg aaggagagcc   1620
ccttcctgtc atgcaggtt gtcgtctggg aacctggagc tacatcatct catttccctc   1680
catctgcaga gtagacagag ggtgaaccac atgggtgcct ttggcattca aggtgcggta   1740
gactagacac catgggcctt gagcctccat caccccctcc caattacctc cacagtttca   1800
caggctgcaa tgccaggcag ctctccacaa cgccatgacc acgagtcaag tgatagctct   1860
tggctagtac agtaatgtcc tgggcattcg cagagtcatg gcagcgttgc tcacaatggc   1920
acccttcttc ccaagccaaa gagtgcatgg tctcactctc ctgggaaaca ccgtggtgat   1980
cgccctccag caaccagctg cctgttggca cccttgttgt ctcctcaagc ttttttatta   2040
tgggaggaa gaagtagtac acattatttt acaggtggac tagtgacatt tgtgatgtct   2100
tattatatta ctctggggat tttatatctt cagaaagtaa ctactcattt ttggtttcca   2160
gttcaacatg taaggagcta agaaatcttt gctccatcct aacagcaagt aaaaagctga   2220
acaaactgaa aaattaacag cccctcttag atccagtaga gaagtgaggt cacaagacaa   2280
actattgttc ccaacattgg agagacagac aggtggggag agagaatcac aacttatctc   2340
cagcagaaac ctccagtgcc agggtaggaa acccgaaaa attgctggag gctcagtgtg   2400
gcaagtctga gggacaaaaa cctccagggg gaccccgtc ctgagggccc ctacactttt   2460
gtgaattta cctccaggag ctcgaccagg tcctcacagt ggatattgtg gtcagcactt   2520
acaggaatgg tccctccaac atctgagcga ggaaggggca cagagcacag ttgtgccttc   2580
cttgggcctg ggcaagctct gtgcttcaca gagcaagcct gtgtcagatc cttcagcaga   2640
gaccacagcc aggggtggtg aagccgatga ggaagtgagg gccaaccaca ctgctcaggc   2700
tgttcctcac aggaggctgg ggcaggctga gccacgcaag accacagctc tcagccctgt   2760
gctatttcca gggcacactt acagatcctg aatggtagag aacgtcctgg ataaaacaat   2820
gacagcaaga cagccatgta cacagatatc ttgtgggaaa ccctttcacg gccactttga   2880
aactgggttg ggagaaggac gtgatgctgg gtcaggcatc cattggggac catggacatt   2940
tttgagagt ttgggccaat gttccttgtgt aatttgtcag aaggaacacc tacttcttca   3000
ttccttgtgaa gaagaaccca taaactggcc cccgtgttca gaggctccag tcgagcgagt   3060
tgaggggaca gctggacttc tccttcctca ggctggctgg aggcttcagc aagggggcac   3120
accgtccaca cgcctctgta aaacagcgtt cgaacggaca atctctaagg catcgtccaa   3180
ctctgagagt ctgtgacctt ccacccctggg gtggagggaa aggccttggg atacagtcca   3240
```

```
cacatcacgt tttcccctaa aagtaccacc cgttttagtc cctgcagaca ctggcctcag    3300
cagcttctct gaggcagccc cgttgagccc agggctgacc acagacaagc actactgtcc    3360
acagaacttc acgcccagtg gggccagact tggaggatgg cagaggagag aagctccagg    3420
ggcctctcca ttagaaacca acttgcaggc cacttaatct cctatgctca gcctgtactt    3480
ggaagctgct tgttcttggc tgcacatttg ctttgtttga atcaattaat ccaagtctct    3540
ctcctctccc cacccccaac cttgccttta gggtgacatc aatattcatg taataaagaa    3600
atcgcacaaa aagctgactc cccacttcct gccctacagg cccttttttc ttcctcagcc    3660
catgtgcaat cctggctccc agcaagtccc cggggctgct tggtcaatgc agccctgtgt    3720
gcaggcctgg cagccctgcc acccccgcct tcggctccca ttggctgcca cggcctgcag    3780
tgggctgcac cagggttcat ccatcctccc tgggcagagg gaataagagg ctgcctctgc    3840
ccaccagtcc tgccgcccag gacccgcagc agagacgacg cctgcagcaa gg            3892

<210> SEQ ID NO 2
<211> LENGTH: 2507
<212> TYPE: DNA
<213> ORGANISM: H. sapiens

<400> SEQUENCE: 2
cagatgtgag ttaagcagtt tgaacaatcg attgattaga cttttgtggc tgctcatttg      60
ggcatgtggc cgagtactgt gctgtcctgg cccacagcgt cctacaggaa gggacgggct     120
gtaagacgtg ggatcttctg aagtcgtcaa atgaaaaaca ctcctgttga gtgaaaaaac     180
aaataggcta atcctatgat ttttttaaaca tttaaacctg acatgatttt attgcaaatt     240
tccaagaatc cttaaaagtt ataaaaagca taatcaaaat aaatatctgt gacagagttc     300
tacaaagggg aaaactcagt tttccttttg agatcttgcc ccagcatcag ttcaaacact     360
tcctcatata tttcaccaag actcagttcc tgagcaagaa accacaggca cagcaagtgc     420
catgaaaagc ggctttgtgt ggggtgggct cttcacactc caatctccac ttccttctca     480
aggcctcaaa aaaagttgaa aaatgaaaac aaaagccctg ctgtgttgag ctgggctctg     540
gcgttgccat ggacccaggg caaacagcgg tgctcctgct ctgcccccgg ctcagctcat     600
gctgggcctg cacttctgga agggagcatg gactttggaa tgactggtta gaacccaaat     660
gaattaatgg aatttgacat agttcaaaaa taataaaatg tgatacccat gaaatgctga     720
tattctgcct taatttgcca gattgggggc ctcctggatt tagagtattc taaagtagcc     780
agtaggttca ctctgcccct ttagacctaa tatatctggc tcagaaagaa gtctctgtcc     840
ctctgctatt tgctgttctt tgctttgccc agtctgactc ctgccagctc caggttctgc     900
agacaagaac agtaactttt ataataataa taatgactcc caagtgagtg cattgggccc     960
ttcacgtgtg tctgtatgtg tgcacatgta tgtgcgtgtc aatttccttt actcctccta    1020
cagccctctc aggggtgcag ctttttttct gtcttttact cagcctgaga aaggttgtcg    1080
tttgacaagg tttgttcaga ggtcggatct gaatccagct ccaaggcccc agcacccaag    1140
ccctgacccc atggctgcct gctggctggg agtggcattc tttagaacag gaaaggcagt    1200
gagttctcat tgcatcaata cttgcatttg ctacaacaga agcttttttgt ctcttcctca    1260 cattccttta gaacacaagc ctcctttttct gcctgtggcc atcggtcact ggagtcagcc    1320
tcgtgagtgg cttggtggcg gatggcaccg tcctttgtgg gagaaaacaa tgttgctgcc    1380
caggcctttc tggaatgacc ccttcccacc ccctgaccag cccagcaag gcccggggct     1440
```

-continued

```
ggctgcctag ttgattggag ccaagagttt gctgaatgga tgaagggaga agggacatcc      1500
aagtgactga agaagatctt aacagaagat tgatatattc aaatagaggc ccctgttgac      1560
ccacaagctc cttcgtgctc tggcctgggc aggcagcact gttgcttggg aaggagagcc      1620
ccttcctgtc atggcaggtt gtcgtctggg aacctggagc tacatcatct catttccctc      1680
catctgcaga gtagacagag ggtgaaccac atgggtgcct ttggcattca aggtgcggta      1740
gactagacac catgggcctt gagcctccat accccctcc caattacctc cacagtttca       1800
caggctgcaa tgccaggcag ctctccacaa cgccatgacc acgagtcaag tgatagctct      1860
tggctagtac agtaatgtcc tgggcattcg cagagtcatg gcagcgttgc tcacaatggc      1920
acccttcttc ccaagccaaa gagtgcatgg tctcactctc ctgggaaaca ccgtggtgat      1980
cgccctccag caaccagctg cctgttggca cccttgttgt ctcctcaagc ttttttatta      2040
ttgggaggaa gaagtagtac acattatttt acaggtggac tagtgacatt tgtgatgtct      2100
tattatatta ctctggggat tttatatctt cagaaagtaa ctactcattt ttggtttcca      2160
gttcaacatg taaggagcta agaaatcttt gctccatcct aacagcaagt aaaaagctga      2220
acaaactgaa aaattaacag cccctcttag atccagtaga gaagtgaggt cacaagacaa      2280
actattgttc ccaacattgg agagacagac aggtggggag agagaatcac aacttatctc      2340
cagcagaaac ctccagtgcc agggtaggaa aacccgaaaa attgctggag gctcagtgtg      2400
gcaagtctga gggacaaaaa cctccagggg gaccccgtc ctgagggccc ctacactttt      2460 gtgaattta cctccaggag ctcgaccagg tcctcacagt ggatatt                    2507
```

<210> SEQ ID NO 3
<211> LENGTH: 1385
<212> TYPE: DNA
<213> ORGANISM: H. sapiens

<400> SEQUENCE: 3

```
gtggtcagca cttacaggaa tggtccctcc aacatctgag cgaggaaggg gcacagagca       60
cagttgtgcc ttccttgggc ctgggcaagc tctgtgcttc acagagcaag cctgtgtcag      120
atccttcagc agagaccaca gccaggggtg gtgaagccga tgaggaagtg agggccaacc      180
acactgctca ggctgttcct cacaggaggc tggggcaggc tgagccacgc aagaccacag      240
ctctcagccc tgtgctattt ccagggcaca cttacagatc ctgaatggta gagaacgtcc      300
tggataaaac aatgacagca agacagccat gtacacagat atcttgtggg aaacccttc      360 acggccactt tgaaactggg ttgggagaag gacgtgatgc tgggtcaggc atccattggg      420
gaccatggac atttttggag agtttgggcc aatgttcttg tgtaatttgt cagaaggaac      480
acctacttct tcattcttgt gaagaagaac ccataaactg cccccgtgt tcagaggctc       540 cagtcgagcg agttgagggg acagctggac ttctccttcc tcaggctggc tggaggcttc      600 agcaagggg cacaccgtcc acacgcctct gtaaaacagc gttcgaacgg acatctcta       660 aggcatcgtc caactctgag agtctgtgac cttccaccct ggggtggagg gaaaggcctt      720
gggatacagt ccacacatca cgttttcccc taaaagtacc cccgttttta gtccctgcag      780
acactggcct cagcagcttc tctgaggcag ccccgttgag cccagggctg accacagaca      840
agcactactg tccacagaac ttcacgccca gtggggccag acttggagga tggcagagga      900
gagaagctcc aggggcctct ccattagaaa ccaacttgca ggccacttaa tctcctatgc      960
tcagcctgta cttggaagct gcttgttctt ggctgcacat ttgctttgtt tgaatcaatt     1020
aatccaagtc tctctcctct ccccaccccc aaccttgcct ttagggtgac atcaatattc     1080
```

```
atgtaataaa gaaatcgcac aaaaagctga ctccccactt cctgccctac aggcccttt    1140 ttcttcctca gcccatgtgc aatcctggct cccagcaagt ccccggggct gcttggtcaa    1200
tgcagccctg tgtgcaggcc tggcagccct gccaccccg ccttcggctc ccattggctg    1260
ccacggcctg cagtgggctg caccagggtt catccatcct ccctgggcag agggaataag    1320
aggctgcctc tgcccaccag tcctgccgcc caggacccgc agcagagacg acgcctgcag    1380
caagg                                                                1385
```